US012729232B2

(12) United States Patent
Davila

(10) Patent No.: US 12,729,232 B2
(45) **Date of Patent: *Sep. 8, 2026**

(54) ARTIFICIAL ANTIGEN PRESENTING CELLS FOR GENETIC ENGINEERING OF IMMUNE CELLS

(71) Applicant: H. LEE MOFFITT CANCER CENTER AND RESEARCH INSTITUTE, INC., Tampa, FL (US)

(72) Inventor: Marco Davila, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 105 days.

This patent is subject to a terminal disclaimer.

(21) Appl. No.: 18/079,302

(22) Filed: Dec. 12, 2022

(65) Prior Publication Data

US 2023/0250151 A1 Aug. 10, 2023

Related U.S. Application Data

(63) Continuation of application No. 16/334,073, filed as application No. PCT/US2017/052152 on Sep. 19, 2017, now Pat. No. 11,524,988.

(Continued)

(51) Int. Cl.

| | |
|---|---|
| ***C07K 14/725*** | (2006.01) |
| ***A61K 40/11*** | (2025.01) |

(Continued)

(52) U.S. Cl.

CPC .......... *C07K 14/7051* (2013.01); *A61K 40/11* (2025.01); *A61K 40/31* (2025.01);

(Continued)

(58) Field of Classification Search

CPC ............ C07K 14/7051; C07K 16/2809; C07K 2317/622; C07K 2319/03; A61K 40/31; A61K 40/4202; C12N 5/0636

See application file for complete search history.

(56) References Cited

U.S. PATENT DOCUMENTS

| | | |
|---|---|---|
| 5,579,250 A | 11/1996 | Balaji et al. |
| 5,612,895 A | 3/1997 | Balaj et al. |

(Continued)

FOREIGN PATENT DOCUMENTS

| | | |
|---|---|---|
| WO | 1995026200 A1 | 10/1995 |
| WO | 1999057150 | 11/1999 |

(Continued)

OTHER PUBLICATIONS

Stock et al. Optimizing Manufacturing Protocols of Chimeric Antigen Receptor T Cells for Improved Anticancer Immunotherapy. Int. J. Mol. Sci. 2019, 20, 6223; doi: 10.3390/ijms20246223 (Year: 2019).*

(Continued)

*Primary Examiner* — Misook Yu
*Assistant Examiner* — Hilary Ann Petrash
(74) *Attorney, Agent, or Firm* — Meunier Carlin & Curfman LLC

(57) ABSTRACT

Disclosed herein are methods of producing chimeric antigen receptor (CAR) T cells using substrates, such as artificial antigen presenting cells, containing on a surface a a heparin binding domain (HBD), anti-CD3 single chain antibodies, anti-CD28 single chain antibodies (scFv), and optionally anti-41BBL antibodies. Anti-CD3 and Anti-CD28 scFvs bind and activate expanding T cells ex vivo, while the Heparin Binding Domain binds the viral vector, thereby bringing the T cells into close proximity with virus for effective gene transfer. This is a less costly, renewable, (Continued)

modifiable, and efficacious alternative to coated beads and RetroNectin® for gene transfer.

20 Claims, 11 Drawing Sheets

Related U.S. Application Data

(60) Provisional application No. 62/400,961, filed on Sep. 28, 2016, provisional application No. 62/396,555, filed on Sep. 19, 2016.

(51) Int. Cl.

| | |
|---|---|
| ***A61K 40/31*** | (2025.01) |
| ***A61K 40/40*** | (2025.01) |
| ***A61K 47/65*** | (2017.01) |
| ***A61P 35/02*** | (2006.01) |
| ***C07K 14/705*** | (2006.01) |
| ***C07K 16/28*** | (2006.01) |
| ***C12N 5/00*** | (2006.01) |
| ***C12N 5/0783*** | (2010.01) |
| ***C12N 15/62*** | (2006.01) |
| ***C12N 15/85*** | (2006.01) |

(52) U.S. Cl.

CPC .............. *A61K 40/40* (2025.01); *A61K 47/65* (2017.08); *A61P 35/02* (2018.01); *C07K 16/2809* (2013.01); *C07K 16/2818* (2013.01); *C12N 5/0075* (2013.01); *C12N 5/0636* (2013.01); *C12N 15/62* (2013.01); *C12N 15/85* (2013.01); *C07K 2317/622* (2013.01); *C07K 2319/03* (2013.01)

(56) References Cited

U.S. PATENT DOCUMENTS

| | | | | |
|---|---|---|---|---|
| 5,631,280 | A | 5/1997 | Ciccarone et al. | |
| 8,008,449 | B2 | 8/2011 | Korman et al. | |
| 8,552,154 | B2 | 10/2013 | Freeman et al. | |
| 8,617,546 | B2 | 12/2013 | Kang et al. | |
| 8,847,356 | B2 | 9/2014 | Saita et al. | |
| 9,493,578 | B2 | 11/2016 | Lazar et al. | |
| 2004/0058447 | A1* | 3/2004 | Ueno | C12N 15/86 435/456 |
| 2004/0101519 | A1* | 5/2004 | June | C12N 5/0634 435/372 |
| 2006/0233787 | A1 | 10/2006 | Le et al. | |
| 2009/0092589 | A1 | 4/2009 | Williams | |
| 2009/0209730 | A1 | 8/2009 | Asada et al. | |
| 2010/0255003 | A1 | 10/2010 | Mevorach et al. | |
| 2014/0011978 | A1 | 1/2014 | Hubbell et al. | |
| 2014/0377270 | A1 | 12/2014 | Moore | |
| 2015/0266939 | A1 | 9/2015 | Vogan et al. | |

FOREIGN PATENT DOCUMENTS

| | | |
|---|---|---|
| WO | 2009132020 | 10/2009 |
| WO | 2011052638 | 5/2011 |

OTHER PUBLICATIONS

Riella et al. Role of the PD-1 Pathway in the Immune Response. American Journal of Transplantation 2012; 12: 2575-2587 (Year: 2012).*

Lamers et al.T Cell Receptor-Engineered T Cells to Treat Solid Tumors: T Cell Processing Toward Optimal T Cell Fitness. Human Gene Therapy Methods 25:345-357 (Dec. 2014) (Year: 2014).*

Kim et al. The ABCs of artificial antigen presentation. Nature Biotechnology vol. 22 Number Apr. 4, 2004 (Year: 2004).*

Hanspal et al. The Association of Erythroblasts With Macrophages Promotes Erythroid Proliferation and Maturation: A 30-kD Heparin-Binding Protein Is Involved in This Contact. Blood, vol. 84, No. 10 (Nov. 15). 1994: pp. 3494-3504 (Year: 1994).*

Butler et al.Human cell-based artificial antigen-presenting cells for cancer immunotherapy Immunol Rev. Jan. 2014 ; 257(1): . doi: 10.1111/imr. 12129 (Year: 2014).*

Turtle et al. Artificial antigen presenting cells for use in adoptive immunotherapy.Cancer J. 2010 ; 16(4): 374-381. (Year: 2010).*

Baneyx et al.Fibronectin extension and unfolding within cell matrix fibrils controlled by cytoskeletal tension PNAS, Apr. 16, 2002 , vol. 99 , No. 8 , 5139-5143 (Year: 2002).*

Non-Final Office Action issued for U.S. Appl. No. 16/487,372, dated Oct. 12, 2023.

Pollok, Karen E., et al. "High-efficiency gene transfer into normal and adenosine deaminase-deficient T lymphocytes is mediated by transduction on recombinant fibronectin fragments." Journal of virology 72.6 (1998): 4882-4892.

Silva, Vieira, Costa, et al. "Novel humanized anti-CD3 antibodies induce a predominantly immunoregulatory profile in human peripheral blood mononuclear cells" Immunology Letters 125 (2009): 129-136.

Wu, Zhijian, et al. "Single amino acid changes can influence titer, heparin binding, and tissue tropism in different adeno-associated virus serotypes." Journal of virology 80.22 (2006): 11393-11397.

Albrecht, Huguette, Gerald L. DeNardo, and Sally J. DeNardo. "Monospecific bivalent scFv-SH: effects of linker length and location of an engineered cysteine on production, antigen binding activity and free SH accessibility." Journal of immunological methods 310.1-2 (2006): 100-116.

Argos, Patrick. "An investigation of oligopeptides linking domains in protein tertiary structures and possible candidates for general gene fusion." Journal of molecular biology 211.4 (1990): 943-958.

Bird, Robert E., et al. "Single-chain antigen-binding proteins." Science 242.4877 (1988): 423-426.

Fauriat, C., F. Mallet, and D. Olive. "Impaired activating receptor expression pattern in natural killer cells from patients with multiple myeloma." Leukemia 20.4 (2006): 732-733.

Feng, Jiannan, et al. "Design and assembly of anti-CD16 ScFv antibody with two different linker peptides." Journal of immunological methods 282.1-2 (2003): 33-43.

Godfrey, James, and Don M. Benson Jr. "The role of natural killer cells in immunity against multiple myeloma." Leukemia & lymphoma 53.9 (2012): 1666-1676.

Griffiths, Andrew D., and Alexander R. Duncan. "Strategies for selection of antibodies by phage display." Current opinion in biotechnology 9.1 (1998): 102-108.

Harlow et al. (Eds.), Antibodies: A Laboratory Manual; Cold Spring Harbor Laboratory; Cold Spring Harbor, N.Y., 1988, Chapter 6.

Holliger, Philipp, and Peter J. Hudson. "Engineered antibody fragments and the rise of single domains." Nature biotechnology 23.9 (2005): 1126.

Huston, James S., et al. "[3] Protein engineering of single-chain Fv analogs and fusion proteins." Methods in enzymology. vol. 203. Academic Press, 1991. 46-88.

International Preliminary Report on Patentability Application No. PCT/US2017/052152, dated Mar. 28, 2019.

International Search Report and Written Opinion issued for Application No. PCT/US2017/052152, dated Dec. 15, 2017.

International Preliminary Report on Patentability Application No. PCT/US2018/019181, dated Aug. 27, 2019.

International Search Report and Written Opinion issued for Application No. PCT/US2018/019181, dated Jun. 15, 2018.

Kumada, Yoichi, et al. "Polypeptide linkers suitable for the efficient production of dimeric scFv in *Escherichia coli*." Biochemical engineering journal 35.2 (2007): 158-165.

Morgan, Richard A., et al. "Case report of a serious adverse event following the administration of T cells transduced with a chimeric antigen receptor recognizing ERBB2." Molecular Therapy 18.4 (2010): 843-851.

Narni-Mancinelli, Emilie, Eric Vivier, and Yann M. Kerdiles. "The 'T-cell-ness' of NK cells: unexpected similarities between NK cells and T cells." International immunology 23.7 (2011): 427-431.

(56) References Cited

OTHER PUBLICATIONS

Porter, David L., et al. "Chimeric antigen receptor-modified T cells in chronic lymphoid leukemia." New England Journal of Medicine 365.8 (2011): 725-733.
Smallshaw, Joan E., et al. "Synthesis, cloning and expression of the single-chain Fv gene of the HPr-specific monoclonal antibody, Jel42. Determination of binding constants with wild-type and mutant HPrs." Protein engineering 12.7 (1999): 623-630.
Takkinen, Kristiina, et al. "An active single-chain antibody containing a cellulase linker domain is secreted by *Escherichia coli*." Protein Engineering, Design and Selection 4.7 (1991): 837-841.
Turtle, Cameron J., and Stanley R. Riddell. "Artificial antigen presenting cells for use in adoptive immunotherapy". Cancer journal 16.4 (2010): 374-381.
Whitlow, Mare, et al. "An improved linker for single-chain Fv with reduced aggregation and enhanced proteolytic stability." Protein Engineering, Design and Selection 6.8 (1993): 989-995.
Butler et al. Human cell-based artificial antigen-presenting cells for cancer immunotherapy.Immunol Rev. Jan. 2014; 257(1): ( Year: 2014).
Stock et al.Optimizing Manufacturing Protocols of ChimericAntigen Receptor T Cells for Improved Anticancer Immunotherapy. Int. J. Mol. Sci. 2019, 20, 6223. (Year: 2019).
Riella, Leonardo V., et al. "Role of the PD-1 pathway in the immune response." American Journal of Transplantation 12.10 (2012): 2575-2587.
Office Action issued for U.S. Appl. No. 16/487,372, dated Jul. 22, 2022.
Office Action issued for U.S. Appl. No. 16/487,372, dated Mar. 16, 2023.
Paul, Fundamental Immunology (textbook), 1993, 292-295.
Green, Bioscience Horizons 2014, 7:1-10.
Lloyd, C., et al. "Modelling the human immune response: performance of a 1011 human antibody repertoire against a broad panel of therapeutically relevant antigens." Protein Engineering, Design & Selection 22.3 (2009): 159-168.
Edwards, Bryan M., et al. "The remarkable flexibility of the human antibody repertoire; isolation of over one thousand different antibodies to a single protein, BLyS." Journal of molecular biology 334.1 (2003): 103-118.
Piche-Nicholas, N. M., Avery, L. B., King, A. C., Kavosi, M., Wang, M., O'Hara, D. M., . . . & Katragadda, M. (Jan. 2018). Changes in complementarity-determining regions significantly alter IgG binding to the neonatal Fc receptor (FcRn) and pharmacokinetics. In MAbs (vol. 10, No. 1, pp. 81-94). Taylor & Francis.
Moritz, Thomas, et al. "Fibronectin improves transduction of reconstituting hematopoietic stem cells by retroviral vectors: evidence of direct viral binding to chymotryptic carboxy-terminal fragments." (1996): 855-862.
Tur, Mehmet Kemal, et al. "In vivo efficacy of the recombinant anti-CD64 immunotoxin H22 (scFv)-ETA' in a human acute myeloid leukemia xenograft tumor model." International journal of cancer 129.5 (2011): 1277-1282.
Yong, Seok-Beom, et al. "Human CD64-targeted non-viral siRNA delivery system for blood monocyte gene modulation." Scientific Reports 7.1 (2017): 42171.

* cited by examiner

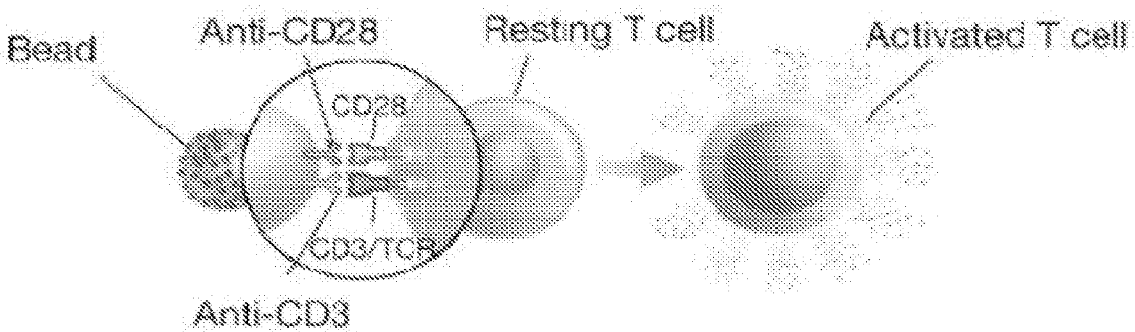
FIG. 2

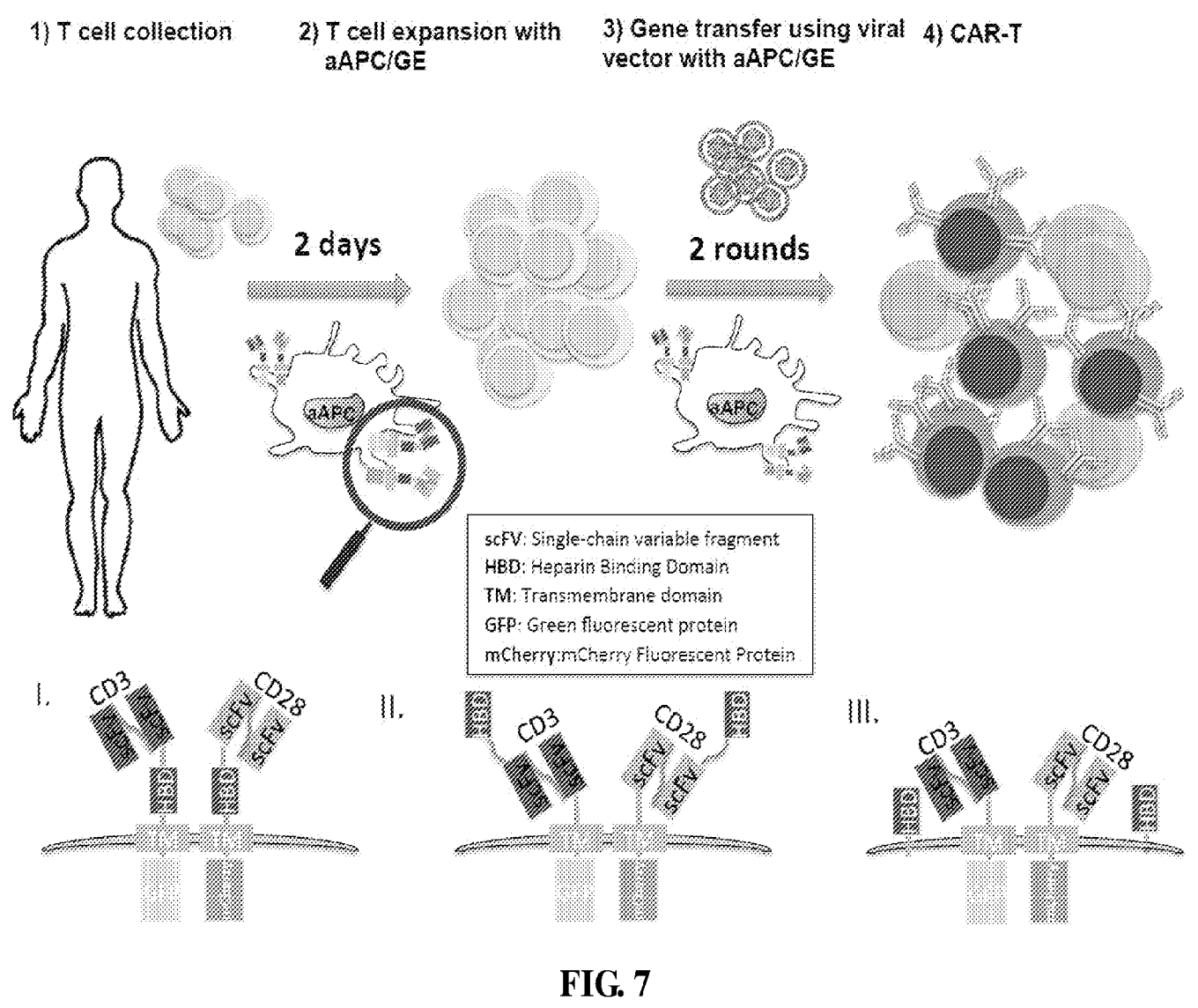

1) T cell collection

2) T cell expansion with aAPC/GE

3) Gene transfer using viral vector with aAPC/GE

4) CAR-T 2 days 2 rounds aAPC scFV: Single-chain variable fragment
HBD: Heparin Binding Domain
TM: Transmembrane domain
GFP: Green fluorescent protein
mCherry: mCherry Fluorescent Protein

I.

II.

III.

CD3

CD28 scFV

HBD

FIG. 7

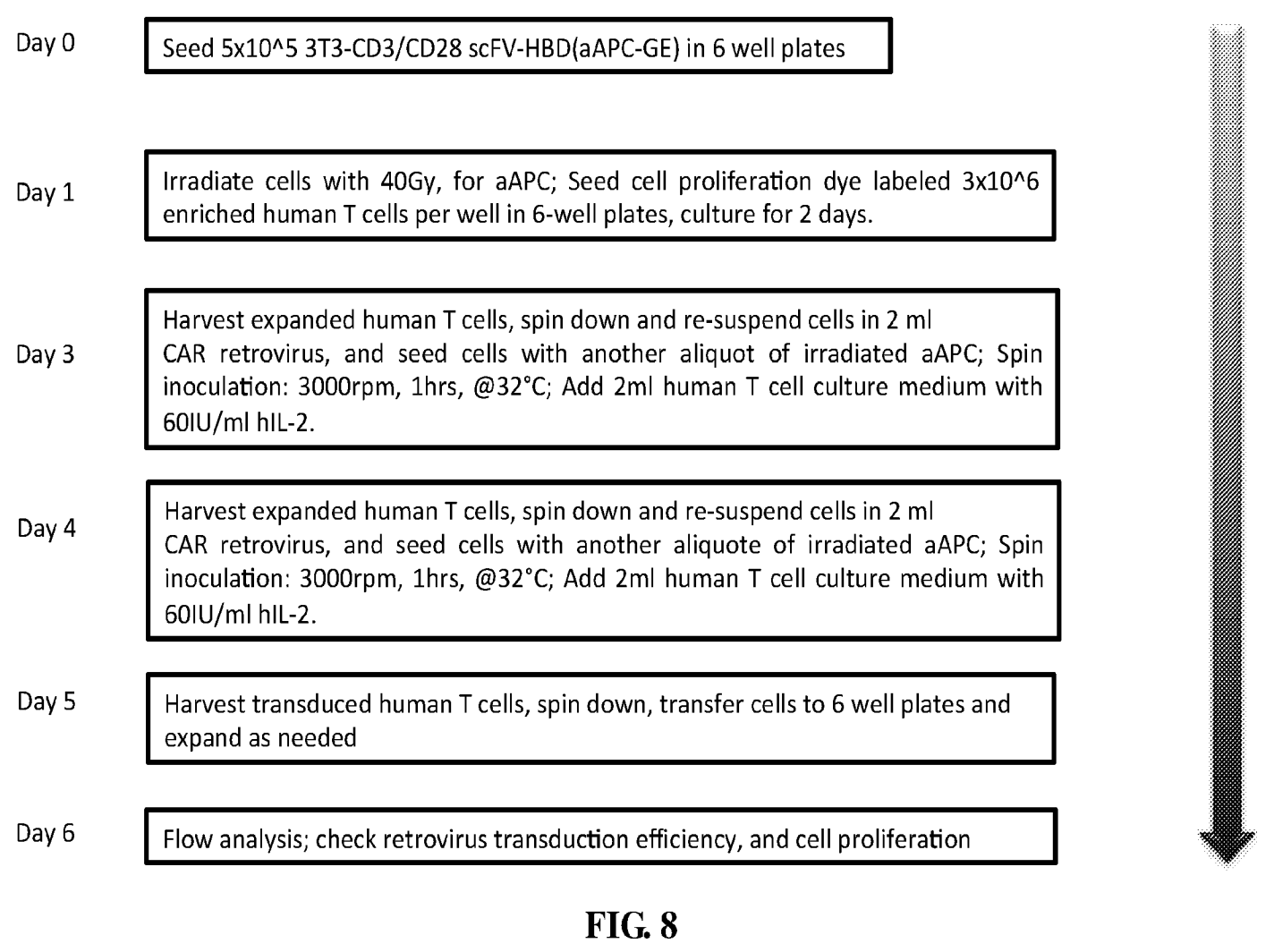

| | |
|---|---|
| Day 0 | Seed 5x10^5 3T3-CD3/CD28 scFV-HBD(aAPC-GE) in 6 well plates |
| Day 1 | Irradiate cells with 40Gy, for aAPC; Seed cell proliferation dye labeled 3x10^6 enriched human T cells per well in 6-well plates, culture for 2 days. |
| Day 3 | Harvest expanded human T cells, spin down and re-suspend cells in 2 ml CAR retrovirus, and seed cells with another aliquot of irradiated aAPC; Spin inoculation: 3000rpm, 1hrs, @32°C; Add 2ml human T cell culture medium with 60IU/ml hIL-2. |
| Day 4 | Harvest expanded human T cells, spin down and re-suspend cells in 2 ml CAR retrovirus, and seed cells with another aliquote of irradiated aAPC; Spin inoculation: 3000rpm, 1hrs, @32°C; Add 2ml human T cell culture medium with 60IU/ml hIL-2. |
| Day 5 | Harvest transduced human T cells, spin down, transfer cells to 6 well plates and expand as needed |
| Day 6 | Flow analysis; check retrovirus transduction efficiency, and cell proliferation |

FIG. 8

ARTIFICIAL ANTIGEN PRESENTING CELLS FOR GENETIC ENGINEERING OF IMMUNE CELLS

CROSS-REFERENCE TO RELATED APPLICATIONS

This application claims benefit of U.S. Provisional Application No. 62/396,555, filed Sep. 19, 2016 and U.S. Provisional Application No. 62/400,961, filed Sep. 28, 2016, incorporated herein by reference in its entirety.

BACKGROUND

Adoptive T cell immunotherapy offers a promising strategy for specifically targeting and eliminating cancerous cells. T cells can be engineered ex vivo to express chimeric antigen receptors specific for tumor antigens (CAR T cells). The expansion and function of adoptively transferred CAR T cells can be potentiated by the lymphodepletive and tumoricidal effects of standard of care chemotherapy and radiotherapy.

Production of CAR T cells currently involves isolation and activation of T cells from peripheral blood mononuclear cell (PBMC) with anti-CD3/anti-CD28 paramagnetic beads. The T cells are added to culture containers pre-treated with RetroNectin® and incubated with viral particles for gene transfer. The cells, beads and virus are incubated and the gene-modified cells are expanded. The beads and RetroNectin® are expensive and are limited in supply. Furthermore, the paramagnetic beads are also limited in their ability to be conjugated with more antibodies to activate and/or co-stimulate immune cells due to their small size.

SUMMARY

Disclosed herein are methods of producing chimeric antigen receptor (CAR) T cells using substrates, such as artificial antigen presenting cells, containing on a surface a a heparin binding domain (HBD), anti-CD3 single chain antibodies, anti-CD28 single chain antibodies (scFv), and optionally anti-41BBL antibodies. Anti-CD3 and Anti-CD28 scFvs bind and activate expanding T cells ex vivo, while the Heparin Binding Domain binds the viral vector, thereby bringing the T cells into close proximity with virus for effective gene transfer. This is a less costly, renewable, modifiable, and efficacious alternative to coated beads and RetroNectin® for gene transfer.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 illustrates critical reagents for prior art GMP CAR-T cell production.

FIG. 7 illustrates an embodiment of the disclosed method for producing CAR-T cells using artificial antigen presenting cell for gene engineering (aAPC/GE).

FIG. 8 is a diagram of a protocol for producing CAR-T cells using artificial antigen presenting cell for gene engineering (aAPC/GE) according to one embodiment.

DETAILED DESCRIPTION

Figure 1:
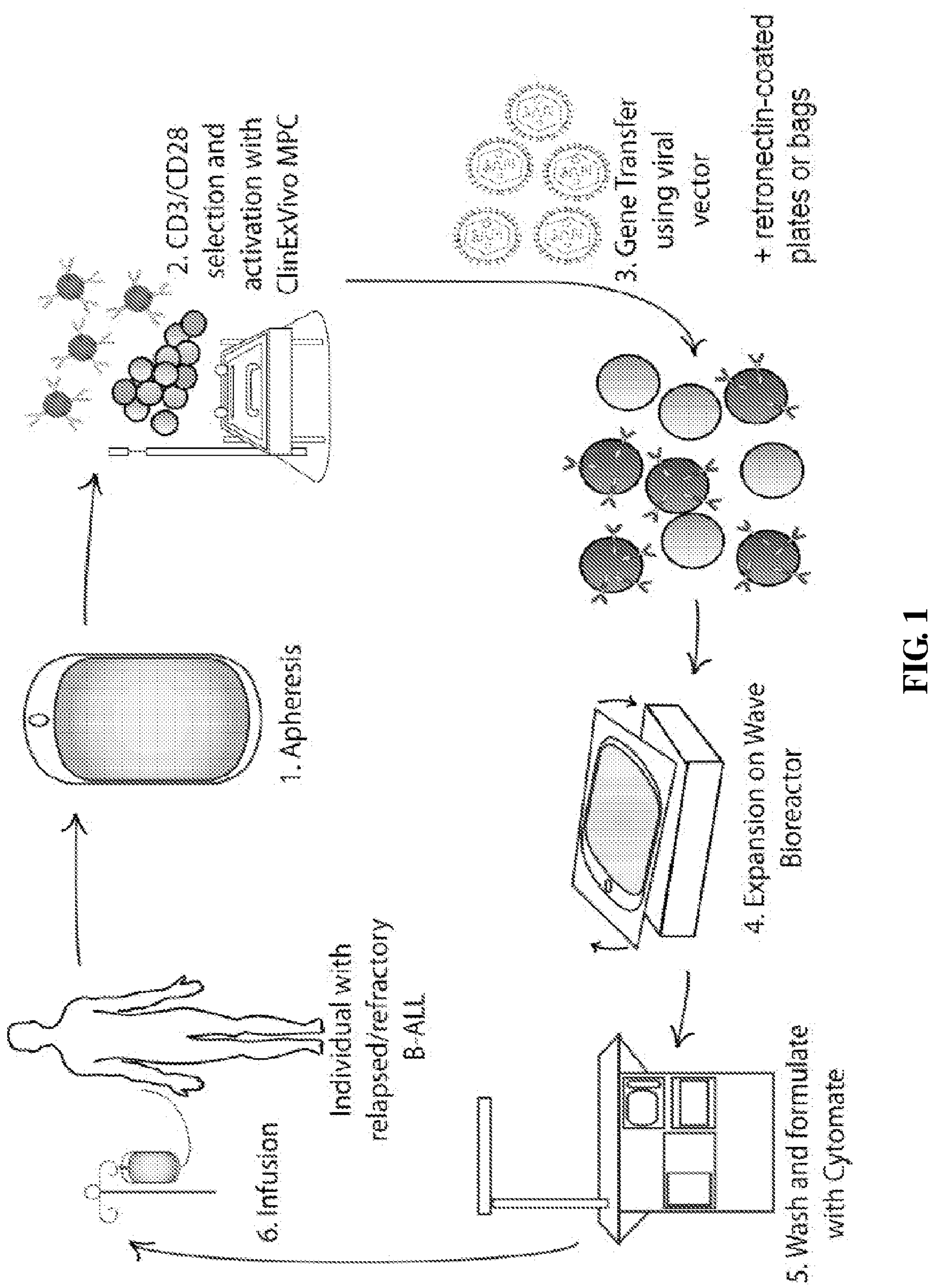
FIG. 1 illustrates the prior art method for CAR T cell production with beads and retronectin.

The term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The term "antibody" refers to natural or synthetic antibodies that selectively hind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively hind the target antigen.

The term "aptamer" refers to oligonucleic acid or peptide molecules that bind to a specific target molecule. These molecules are generally selected from a random sequence pool. The selected aptamers are capable of adapting unique tertiary structures and recognizing target molecules with high affinity and specificity. A "nucleic acid aptamer" is a DNA or RNA oligonucleic acid that binds to a target molecule via its conformation, and thereby inhibits or suppresses functions of such molecule. A nucleic acid aptamer may be constituted by DNA, RNA, or a combination thereof. A "peptide aptamer" is a combinatorial protein molecule with a variable peptide sequence inserted within a constant scaffold protein. Identification of peptide aptamers is typically performed under stringent yeast dihybrid conditions, which enhances the probability for the selected peptide aptamers to be stably expressed and correctly folded in an intracellular context.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "chimeric molecule" refers to a single molecule created by joining two or more molecules that exist separately in their native state. The single, chimeric molecule has the desired functionality of all of its constituent molecules. One type of chimeric molecules is a fusion protein.

The term "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "peptide," "protein," and "polypeptide" are used interchangeably to refer to a natural or synthetic molecule comprising two or more amino acids linked by the carboxyl group of one amino acid to the alpha amino group of another.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "protein domain" refers to a portion of a protein, portions of a protein, or an entire protein showing structural integrity; this determination may be based on amino acid composition of a portion of a protein, portions of a protein, or the entire protein.

A "spacer" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells hearing the target molecule than between the delivered molecule and cells lacking the target molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The terms "transformation" and "transfection" mean the introduction of a nucleic acid, e.g., an expression vector, into a recipient cell including introduction of a nucleic acid to the chromosomal DNA of said cell.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "variant" refers to an amino acid or peptide sequence having conservative amino acid substitutions, non-conservative amino acid subsitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, 95%, 96%, 97%, 98%, 99% sequence identity to a reference sequence.

The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element).

The disclosed aAPC can incorporate an antigen recognition domain from the single-chain variable fragments (scFv) of a monoclonal antibody (mAb) that specifically binds an antigen on an immune effector cell.

Immune effector cells are preferably obtained from the subject to be treated (i.e. are autologous). However, in some embodiments, immune effector cell lines or donor effector cells (allogeneic) are used. Immune effector cells can be obtained from a number of sources, including peripheral blood mononuclear cells, bone marrow, lymph node tissue, cord blood, thymus tissue, tissue from a site of infection, ascites, pleural effusion, spleen tissue, and tumors. Immune effector cells can be obtained from blood collected from a subject using any number of techniques known to the skilled artisan, such as Ficoll™ separation. For example, cells from the circulating blood of an individual may be obtained by apheresis. In some embodiments, immune effector cells are isolated from peripheral blood lymphocytes by lysing the red blood cells and depleting the monocytes, for example, by centrifugation through a PERCOLL™ gradient or by counterflow centrifugal elutriation. A specific subpopulation of immune effector cells can be further isolated by positive or negative selection techniques. For example, immune effector cells can be isolated using a combination of antibodies directed to surface markers unique to the positively selected cells, e.g., by incubation with antibody-conjugated beads for a time period sufficient for positive selection of the desired immune effector cells. Alternatively, enrichment of immune effector cells population can be accomplished by negative selection using a combination of antibodies directed to surface markers unique to the negatively selected cells.

In some embodiments, the immune effector cells comprise any leukocyte involved in defending the body against infectious disease and foreign materials. For example, the immune effector cells can comprise lymphocytes, monocytes, macrophages, dentritic cells, mast cells, neutrophils, basophils, eosinophils, or any combinations thereof. For example, the the immune effector cells can comprise T lymphocytes.

T cells or T lymphocytes can be distinguished from other lymphocytes, such as B cells and natural killer cells (NK cells), by the presence of a T-cell receptor (TCR) on the cell surface. They are called T cells because they mature in the thymus (although some also mature in the tonsils). There are several subsets of T cells, each with a distinct function.

T helper cells ($T_H$ cells) assist other white blood cells in immunologic processes, including maturation of B cells into plasma cells and memory B cells, and activation of cytotoxic T cells and macrophages. These cells are also known as CD4+ T cells because they express the CD4 glycoprotein on their surface. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H17$, $T_H9$, or $T_{FH}$, which secrete different cytokines to facilitate a different type of immune response.

Cytotoxic T cells ($T_C$ cells, or CTLs) destroy virally infected cells and tumor cells, and are also implicated in transplant rejection. These cells are also known as $CD8^+$ T cells since they express the CD8 glycoprotein at their surface. These cells recognize their targets by binding to antigen associated with MHC class I molecules, which are present on the surface of all nucleated cells. Through IL-10, adenosine and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory cells may be either CD4+ or CD8+. Memory T cells typically express the cell surface protein CD45RO.

Regulatory T cells ($T_{reg}$ cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus. Two major classes of $CD4^+$ $T_{reg}$ cells have been described—naturally occurring $T_{reg}$ cells and adaptive $T_{reg}$ cells.

Natural killer T (NKT) cells (not to be confused with natural killer (NK) cells) bridge the adaptive immune system with the innate immune system. Unlike conventional T cells that recognize peptide antigens presented by major histocompatibility complex (MHC) molecules, NKT cells recognize glycolipid antigen presented by a molecule called CD1d.

In some embodiments, the T cells comprise a mixture of CD4+ cells. In other embodiments, the T cells are enriched for one or more subsets based on cell surface expression. For example, in some cases, the T comprise are cytotoxic $CD8^+$ T lymphocytes. In some embodiments, the T cells comprise $\gamma\delta$T cells, which possess a distinct T-cell receptor (TCR) having one $\gamma$ chain and one $\delta$ chain instead of $\alpha$ and $\beta$ chains.

Natural-killer (NK) cells are $CD56^+CD3^-$ large granular lymphocytes that can kill virally infected and transformed cells, and constitute a critical cellular subset of the innate immune system (Godfrey J, et al. Leuk Lymphoma 2012 53:1666-1676). Unlike cytotoxic CD8+ T lymphocytes, NK cells launch cytotoxicity against tumor cells without the requirement for prior sensitization, and can also eradicate MHC-I-negative cells (Narni-Mancinelli E, et al. Int Immunol 2011 23:427-431). NK cells are safer effector cells, as they may avoid the potentially lethal complications of cytokine storms (Morgan R A, et al. Mol Ther 2010 18:843-851), tumor lysis syndrome (Porter D L, et al. N Engl J Med 2011 365:725-733), and on-target, off-tumor effects. Although NK cells have a well-known role as killers of cancer cells, and NK cell impairment has been extensively documented as crucial for progression of MM (Godfrey J, et al. Leuk Lymphoma 2012 53:1666-1676; Fauriat C, et al. Leukemia 2006 20:732-733), the means by which one might enhance NK cell-mediated anti-MM activity has been largely unexplored prior to the disclosed CARs.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Protocol for Human T Cell Expansion/Transduction with Gene Engineering aAPC (aAPC/GE)

1. Preparation of aAPC/GE Cells (Day 0, 1)

NIH-3T3 cells were engineered by gene transduction with retrovirus, which express CD3-scFV-HBD and CD28-scFV-HBD. These gene engineered NIH-3T3 cells were used as artificial antigen presenting cells to support T cell expansion and CAR gene transduction, a. aAPC/GE with 90% confluency in 10 cm culture dishes were washed once with PBS; 3 ml 0.5% Trypsin-EDTA were added to detach adherent aAPC/GE cells. After neutralization with 10% FCS DMEM culture medium, aAPC/GE cells were spin down, 400 G×5 mins; and re-suspended with 10% FCS DMEM culture medium;

b. Count cells and seed aAPC/GE 3×10ˆ5/2 ml/well in 6 well tissue culture plates;

c. One day later, cell confluency reach 80%; Put cell culture plate in the chamber for irradiation with a dose of 40000 ray;

d. Incubate in a tissue culture incubator at 37° C. (5% CO2)

2. T Cell Proliferation (Day 1-3)

a. Human T cells were enriched from PBMC using EasySep™ Human T Cell Enrichment Kit (Catalog #19051, STEMCELL Technologies Inc); T cell were labeled with cell proliferation dye (Catlog # 65-0842-85, ebioscience) and suspended in human T cell culture medium (10% FCS RPMI 1640 with 30 IU/mL of hIL-2)

b. Remove DMEM culture medium in aAPC/GE plates and add 3×10ˆ6/2 ml 1/well enriched human T cells to the aAPC/GE;

c. Incubate in a tissue culture incubator at 37° C. (5% CO2). T cell proliferate rapidly after 2 days co-culture.

3. T Cell Transduction (Day 3, 4)

a. Day 3, Harvest expanded human T cells, spin down 400 G×5 mins; Resuspend cell pellets with 2 ml retrovirus, and seed cells over the irradiated aAPC/GE in 6 well tissue culture plates; Spin inoculation: 2000 G, 1 hrs, at 32° C.; After spin inoculation, add 2 ml human T cell culture medium with 60 IU/ml hIL-2.

b. Day 4, repeat the above procedure, do another round spin-inoculation;

4. T Cell Transduction Analysis at day 7 a. Day 5, Harvest suspened human T cells, spin down 400 G×5 mins; Resuspend with human T cell culture medium containing 30 IU/ml hIL-2.

b. Continue culture for another 2 days.

c. Harvest transduced cell and wash with PBS. Cell is ready for flow cytometry assay of T cell proliferation and transduction efficiency.

FIG. 1 is a schematic of standard methods of gene-engineering T cells. 1) Peripheral, circulating cells are collected from a patient by leukapheresis. 2) T cells are both isolated and activated by incubation with CD3/CD28 magnetic beads followed by exposure of the cells and beads to a magnet. 3) Activated T cells are incubated with virus and retronectin-coated bags or plates to facilitate viral-mediated gene transfer. After viral transfer, the cells are expanded (4), washed (5), and infused back into the patient.

FIG. 2 (top panel) is a schematic of CD3/CD28 isolation and activation beads which binds T cell proteins CD3 and CD28. This supports activation of a resting T cell. Retronectin is used to coat bags and/or plates to facilitate viral transduction of cells (FIG. 2, bottom panel).

Figure 3:
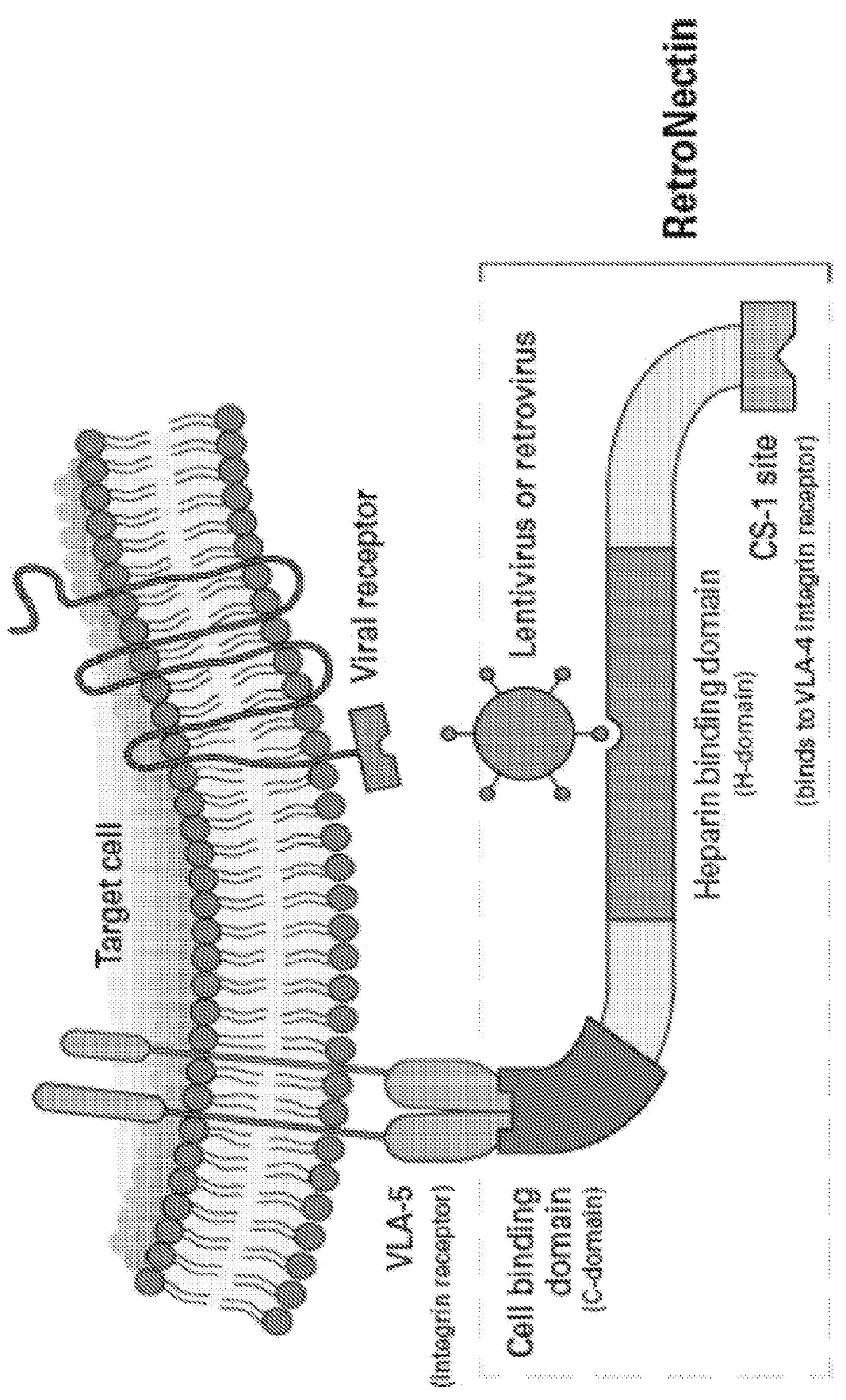
FIG. 3 illustrates how RetroNectin binds T cells and virus.

Retronectin facilitates viral transduction of cells by bringing the virus and target cell into close proximity of each other (FIG. 3). The retronectin protein includes a Cell binding domain that binds VLA-5 and a heparin binding domain (HBD) that binds virus.

Figure 4:
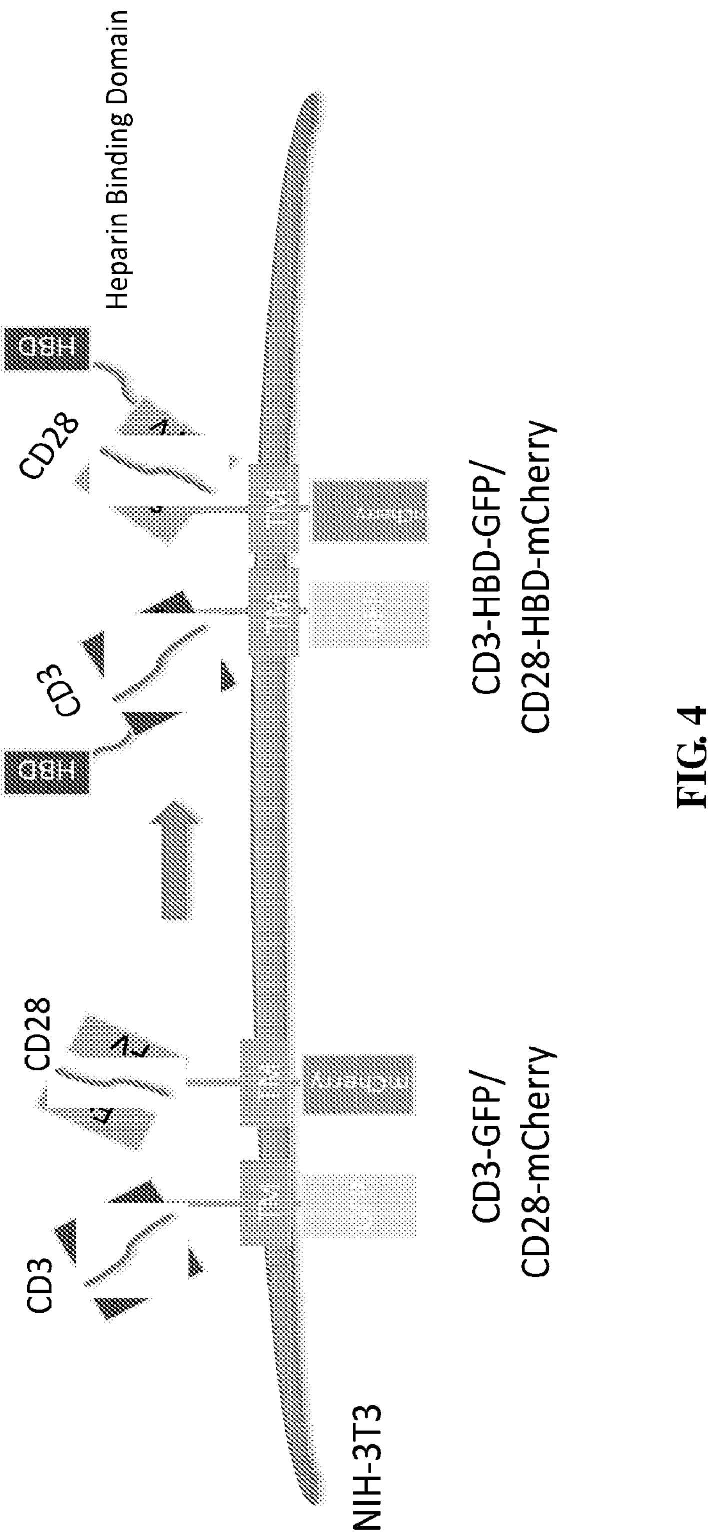
FIG. 4 illustrates an embodiment of the disclosed artificial antigen presenting cell for gene engineering (aAPC/GE).

FIG. 4 is a schematic of NIH-3T3 cells expressing AAPCs for Gene-Engineering (AAPC/GE). The scFv are anchored in the cell membrane with a transmembrane domain and intracellular domains include fluorescent proteins for monitoring cells by flow cytometry. The heparin binding domain (HBD) is present at the N-terminal domain of the protein and assist with viral binding.

Figure 5:
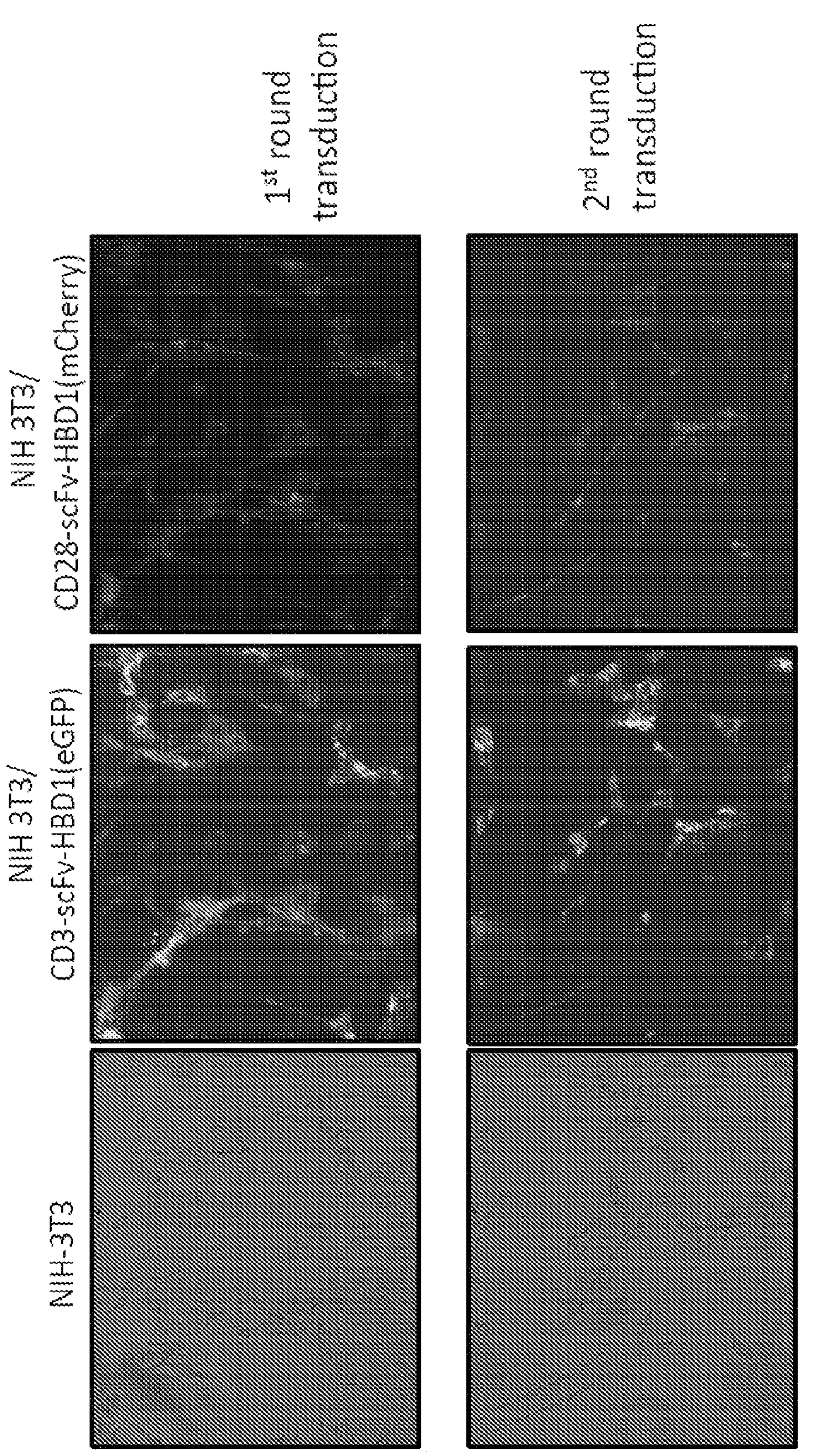
FIG. 5 shows transduction of NIH/3T3 cells with CD3-HBD/CD28-HBD retrovirus.

NIH-3T3 cells are transduced to express scFv and HBD (FIG. 5). NIH-3T3 cells were transduced two times with CD3-scFV-HBD(GFP) construct, followed by two times with the CD28-scFv-HBD(cherry) construct. Successful gene-transfer is confirmed by fluorescent microscopy for GFP and Cherry fluorescence.

Figure 6:
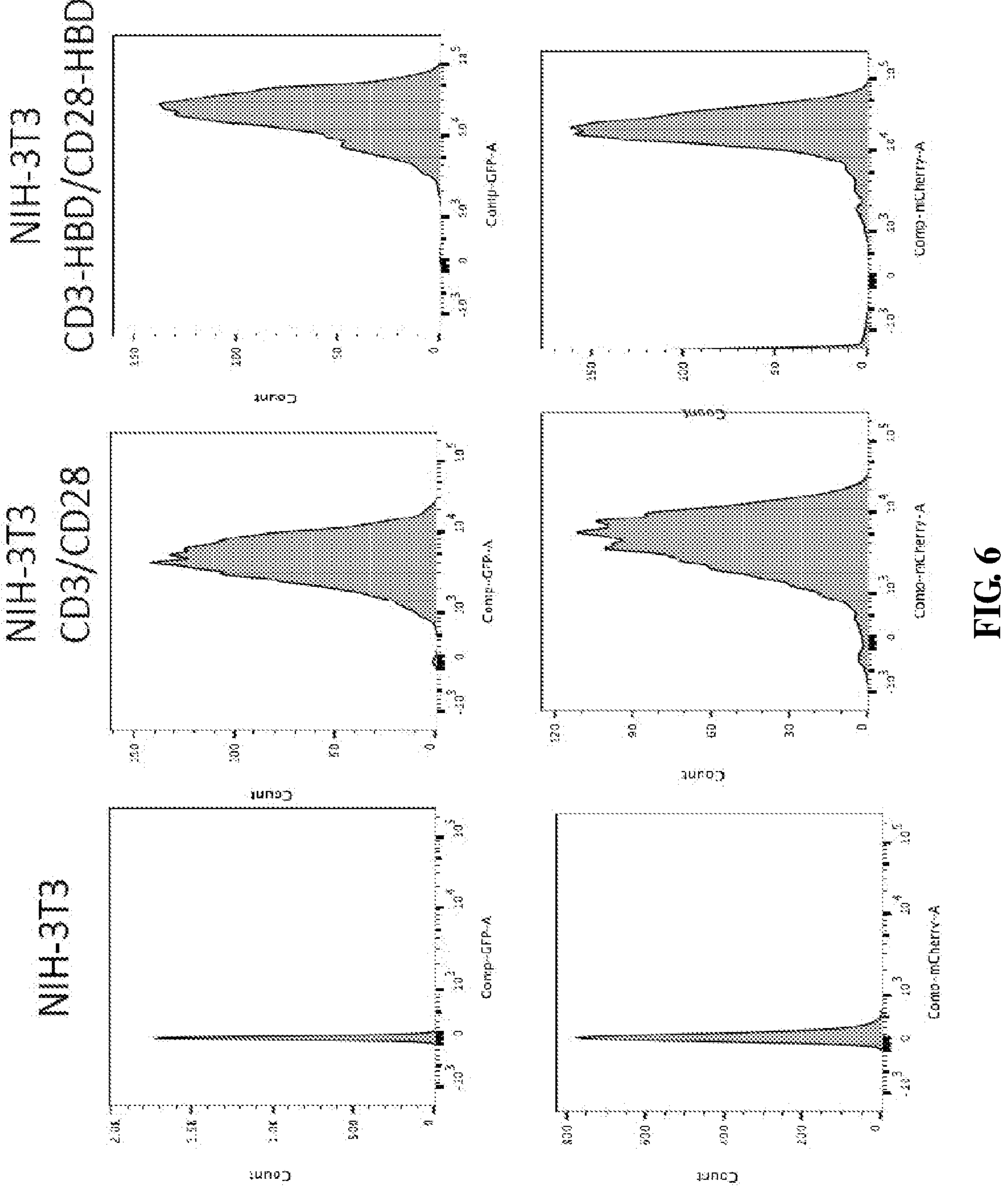
FIG. 6 shows flow cytometry of transduced NIH-3T3 with CD3-HBD and CD28-HBD.

NIH-3T3 cells are transduced to express scFv and/or HBD (FIG. 6). NIH-3T3 cells were transduced with CD3-scFV-HBD(GFP) followed by CD28-scFv-HBD(cherry). To create a control cell line NIH-3T3 cells were also transduced with CD3-scFV-(GFP) followed by CD28-scFv-(cherry), so this cell line lacks the HBD. Successful gene-transfer is confirmed by flow cytometry for GFP and Cherry fluorescence.

FIG. 7 is a schematic of the refined methods of gene-engineering T cells with AAPC/GE. 1) Peripheral, circulating cells are collected from a patient and T cells are enriched by Ficoll gradient centrifugation or isolated by antibody-mediated negative selection. 2) T cells are activated by incubation with AAPC/GE. 3) Activated T cells are incubated with virus and AAPC/GE to facilitate viral-mediated gene transfer. After viral transfer, the cells are expanded until time for infusion (4). The bottom panel lists three variants of AAPC/GE: I. with the HBD located after the scFv, II. with HBD at the N-terminal domain, and III. with the HBD separate of the scFv protein.

FIG. 8 is a brief outline of protocol using AAPC/GE to gene-engineer T cells.

Figure 9:
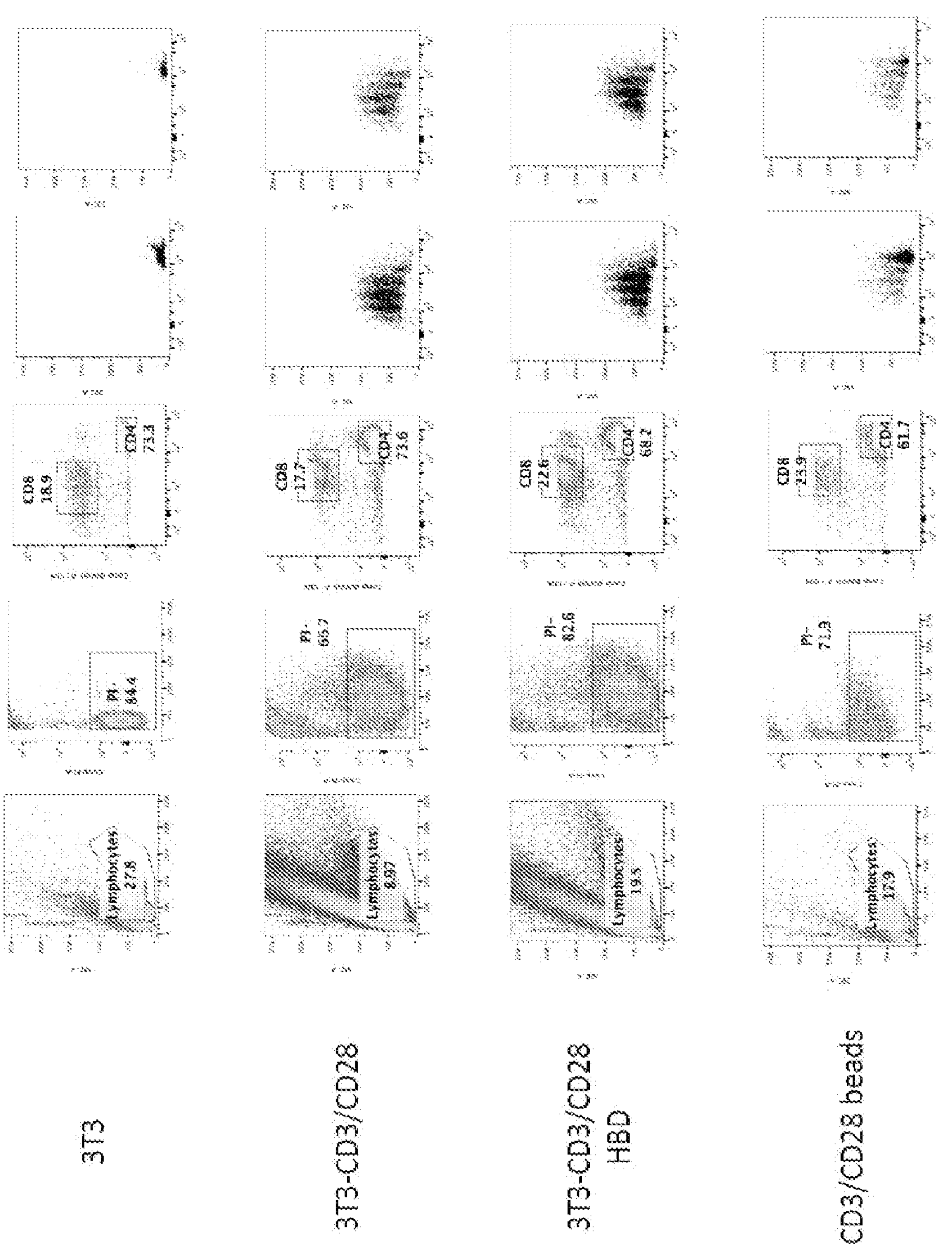
FIG. 9 is a series of flow cytometry graphs showing aAPC/GE stimulate human T cell proliferation at day 6.

Proliferation of T cells stimulated with AAPC/GE or CD3/CD28 activation heads (FIG. 9). T cells were isolated on Day 0 and incubated with a fluorescent dye that is diluted with successive cell proliferation. T cells were then stimulated with CD3/CD28 beads on Day 0 or AAPC/GE on Days 0, 1, 2, and 3. On Day 6 T cells were analyzed for Live/Dead, CD4/CD8 ratio, and finally for evidence of proliferation. The far two right panels illustrate cell proliferation, i.e. dilution of dye, within the CD4 and CD8 compartments.

Figure 10:
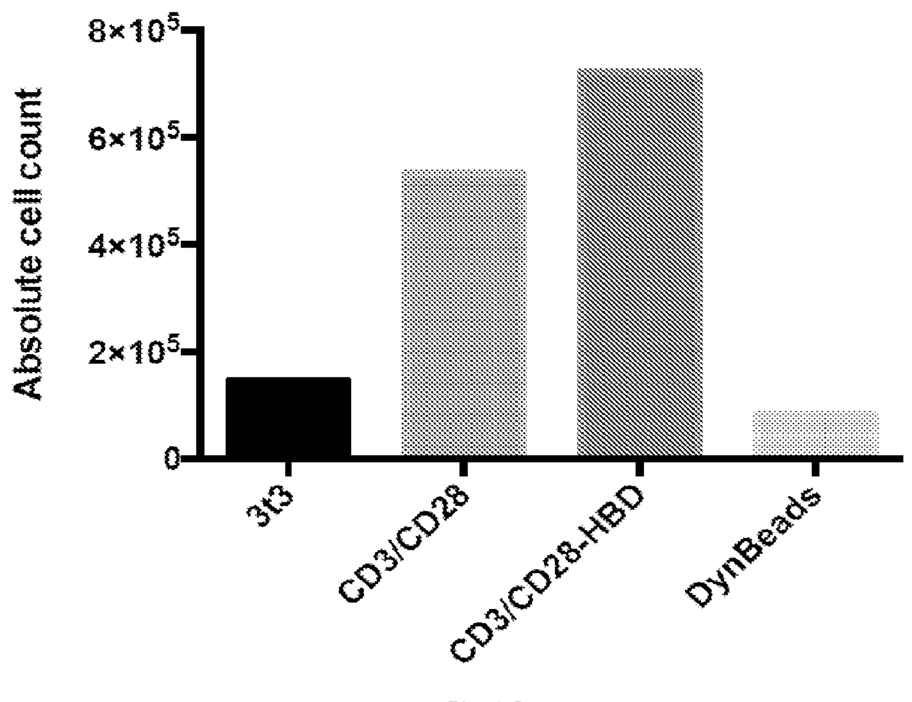
FIG. 10 is a bar graph showing human T cell counts after aAPC stimulation.

Proliferation of T cells stimulated with AAPC/GE or CD3/CD28 activation beads (FIG. 10). T cells were isolated and activated as in FIGS. 8 and 9. Cells were counted on Day 6 to compare total expansion.

Figure 11:
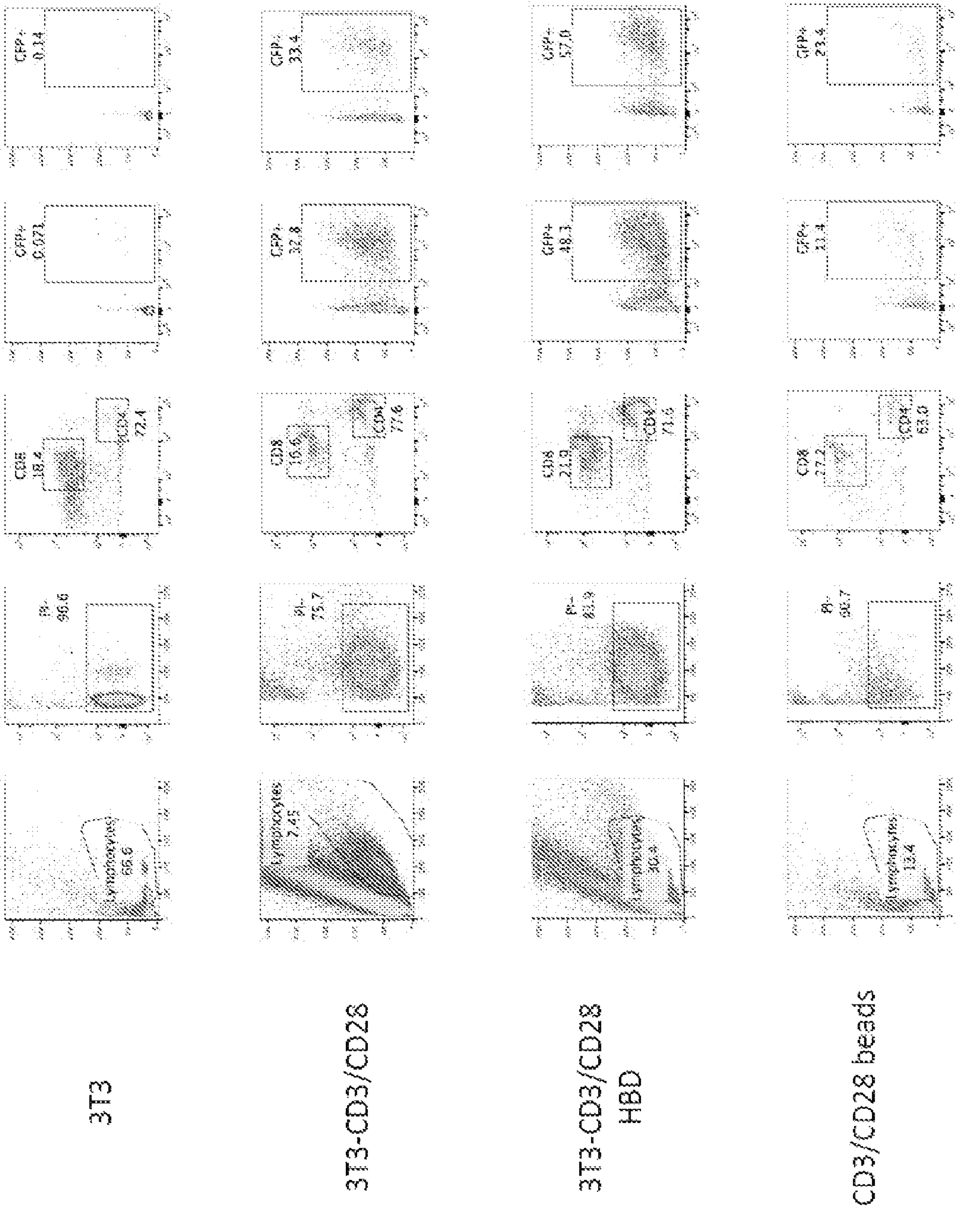
FIG. 11 is a series of flow cytometry graphs showing aAPC/GE support retrovirus transduction of human T cells with CARs at day 6.

Proliferation of T cells stimulated with AAPC/GE or CD3/CD28 activation beads (FIG. 11). T cells were isolated and activated as in FIGS. 8 and 9. Briefly, T cells were isolated on Day 0 and T cells were stimulated with CD3/CD28 beads on Day 0 or AAPC/GE on Days 0, 1, 2, and 3. On Days 1 and 2 for the CD3/CD28 activated bead group, the T cells were infected with a viral construct that included a CAR tagged to GFP. On Days 2 and 3 for the AAPC/GE activated group, the T cells were infected with a viral construct that included a CAR tagged to GFP. On Day 6 T cells were analyzed for Live/Dead, CD4/CD8 ratio, and finally for evidence of CAR gene transfer by GFP fluorescence. The far two right panels illustrate gene-transfer within the CD4 and CD8 T cell compartments.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for producing chimeric antigen receptor (CAR) T cells comprising a) providing a fusion protein on an exposed surface of a substrate or on a lipid membrane, wherein the fusion protein comprises a heparin binding domain and one or more single chain variable fragments (scFv) comprising an antigen recognition domain that selectively binds a CD3 antigen and/or a CD28 antigen, and b) co-culturing a T cell, a viral vector encoding a chimeric antigen receptor, and an effective amount of the-fusion protein.

2. The method of claim 1, wherein the fusion protein is expressed on the lipid membrane of a cell line.

3. The method of claim 2, wherein the cell line comprises an artificial antigen presenting cell (aAPC).

4. The method of claim 3, wherein the cell line comprises an NIH/3T3 cell line.

5. The method of claim 1, wherein the substrate comprises a polymeric or glass container.

6. The method of claim 5, wherein the container comprises a plate, dish, or well.

7. The method of claim 1, wherein the substrate comprises a polymeric or glass particle.

8. The method of claim 7, wherein the particle comprises a bead.

9. The method of claim 8, wherein the particle comprises a paramagnetic bead.

10. The method of claim 1, wherein the heparin binding domain and scFv are present in the same polypeptide.

11. The method of claim 1, wherein the antigen recognition domain selectively binds CD3 receptors.

12. The method of claim 1, wherein the antigen recognition domain binds CD28 receptors.

13. The method of claim 1, wherein the viral vector further comprises an scFV comprising an antigen recognition domain that binds 41BB, glucocorticoid-induced tumor necrosis factor-related receptor (GITR), CTLA4, PD-1, ICOS, CD25, TIM3, LAG3, PD1, CD40, CD137, OX40, CD2, LFA-1, CD28, CD154, BTLA, CD160, TIM 1, TIM 4, or any combination thereof.

14. The method of claim 1, wherein the viral vector further comprises an scFV comprising an antigen recognition domain that binds IL2, IL7, IL12, IL15, IL18, IL10, or any combination thereof.

15. The method of claim 1, wherein the substrate further contains on its surface an scFv comprising an antigen recognition domain that selectively binds a co-stimulatory molecule on T-cells.

16. The method of claim 15, wherein the co-stimulatory molecule comprises 4-1BB.

17. The method of claim 1, comprising a first scFv comprising the formula:

CD3-HBD-TM-ID, or

HBD-CD3-TM-ID, wherein "CD3" comprises a CD3-antigen recognition domain, wherein "HBD" comprises a heparin binding domain, wherein "TM" comprises a transmembrane domain, wherein "ID" comprises an optional intracellular domain, and wherein "38 represents a peptide linker.

18. The method claim 1, comprising a first scFV comprising the formula:

CD28-HBD-TM-ID, or

HBD-CD28-TM-ID, wherein "CD28" comprises a CD28-antigen recognition domain, wherein "HBD" comprises a heparin binding domain, wherein "TM" comprises a transmembrane domain, and wherein "ID" comprises an optional intracellular domain.

19. The method of claim 1, wherein the T cell is a $CD3^+$ T cell.

20. The method of claim 1, wherein the T cell is a NK-T cells, cytokine-induced killer cell, tumor-infiltrating lymphocyte (TIL), marrow-infiltrating lymphocyte, and/or γδT cell.

* * * * *